United States Patent [19]

Leigh

[11] 4,391,983
[45] Jul. 5, 1983

[54] CARBOXAMIDOESTERS

[75] Inventor: Thomas Leigh, Alderley Edge, England

[73] Assignee: Imperial Chemical Industries PLC, London, England

[21] Appl. No.: 62,190

[22] Filed: Jul. 30, 1979

Related U.S. Application Data

[63] Continuation of Ser. No. 803,237, Jun. 3, 1977, abandoned.

[30] Foreign Application Priority Data

Jun. 16, 1976 [GB] United Kingdom ............... 24931/76
Jun. 16, 1976 [GB] United Kingdom ............... 24932/76

[51] Int. Cl.³ .......................................... C07C 69/743
[52] U.S. Cl. .................................. 560/124; 424/305; 424/306; 424/308; 560/105
[58] Field of Search .......................................... 560/124

[56] References Cited

U.S. PATENT DOCUMENTS 4,045,575  8/1977  Searle .................................. 560/124

Primary Examiner—Michael L. Shippen
Attorney, Agent, or Firm—Cushman, Darby & Cushman

[57] ABSTRACT

Esters of formula:

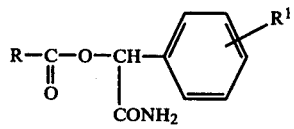

(I)

wherein R is either (a) or a group of formula:

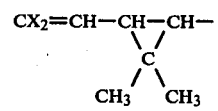

(A)

where X is methyl, chlorine or bromine, or (b) a group of formula:

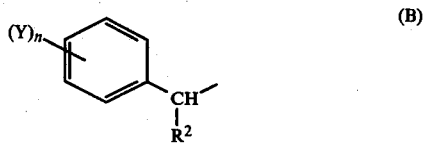

(B)

where Y is methyl or chlorine and n is one or two, and $R^2$ is alkyl or 2 to 4 carbon atoms; and $R^1$ is phenoxy or 2,2-dichlorovinyloxy.

1 Claim, No Drawings

CARBOXAMIDOESTERS

This is a continuation of application Ser. No. 803,237 filed June 3, 1977 now abandoned.

This invention relates to carboxamidoesters, useful as precursors for insecticides and to methods for their preparation.

Elliott et al (nature (1974), 248, 710) has reported the isolation of the insecticide (S)-α-cyano-3-phenoxybenzyl (IR, cis)-3-(2,2-dibromovinyl)-2,2-dimethylcyclopropane carboxylate, by crystallisation from the mixture of the two diastereoisomers which were obtained by esterifying (IR, cis)-3-(2,2-dibromovinyl)-2,2-dimethylcyclopropane carboxylic acid with racemic α-cyano-3-phenoxybenzyl alcohol. The corresponding mixture of dichlorovinyl compounds has been prepared (Elliott et al, Pesticide Sci (1975), 6, 537) but the constituennt corresponding to the above dibromovinyl compound has not been isolated. It may be inferred that this dichlorovinyl derivative will also be a very potent insecticide. It is desirable therefore to prepare the isolated individual dichlorovinyl diastereoisomers viz (S)-α-cyano and (R)-α-cyano-3-phenoxybenzyl (1R, cis)-3-(2,2-dichlorovinyl)-2,2-dimethylcyclopropane carboxylates for evaluation as insecticides.

A preliminary examination of the mixture of diastereoisomers, an oil, indicated that separation by physical methods might be difficult. Obviously the most direct method for the production of the two isomers would be to esterify thhe cyclopropane carboxylic acid with the two enantiomers of α-cyano-3-phenoxybenzyl alcohol. Of the latter the (R) form has been prepared by Elliott et al (Nature (1974), 248, 710) by asymmetric addition of hydrogen cyanide to 3-phenoxybenzaldehyde in the presence of the enzyme D-oxynitrilase. Resolution of a cyanhydrin by the usual resolution techniques, for example via a diastereoisomeric precursor, has not been achieved. It is likely that the conditions necessary for the liberation of the cyanhydrin from a diastereoisomeric precursor will also racemise the cyanhydrin. Optically active benzaldehyde cyanhydrin, for example is known to racemise under extremely mild conditions.

However methods involving enzyme treatment even if effective on the small scale are not really suitable for manufacture. We have therefore devised an alternative technique, utilising novel carboxamidoesters which does not rely upon enzyme treatments.

Accordingly the present invention provides novel esters of formula:

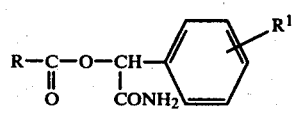

wherein R is either (a) a group of formula:

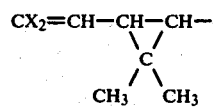

where X is methyl, chlorine or bromine, or (b) a group of formula:

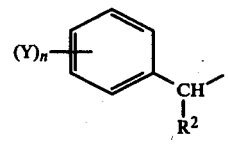

where Y is methyl or chlorine and n is one or two, and $R^2$ is alkyl of 2 to 4 carbon atoms; and $R^1$ is phenoxy or 2,2-dichlorovinyloxy.

A preferred group of esters within the invention comprises compounds of Formula I wherein R is a group of Formula A where X is chlorine or bromine and $R^1$ is 3-phenoxy or 3-(2,2-dichlorovinyloxy).

It will be appreciated by those skilled in the art that in the compounds of Formula I the carbon atom bearing the carboxamido group is substituted by four different atoms or groups and is thus a centre of optical asymmetry, that is the compounds exist in two isomeric forms, having (R) and (S) configurations about this carbon atom. The group R in Formula I contains one or more further centres of optical asymmetry which will give rise to yet further isomeric possibilities. Thus when R is a group of Formula A there are two further optically active centres in the cyclopropane ring giving rise to isomeric forms and there is one such centre in the group of Formula B. Thus in the case of a compound of Formula I where R is a group of Formula A there is a total of eight individual stereoisomeric forms, and in the case of a compound of formula I where R is a group of Formula B there is a total of four individual stereoisomeric forms. It is to be understood that the scope of this invention extends to include all the individual isomers of the compounds of Formula I as well as mixtures thereof including racemates.

Particular compounds which are typical examples of compounds embraced by the invention include the following:

(±)-α-carboxamido-3-phenoxybenzyl (±)cis-trans-3-(2,2-dichlorovinyl)-2,2-dimethylcyclopropane carboxylate, (S)-α-carboxamido-3-phenoxybenzyl (1R,3S)-3-(2,2-dichlorovinyl)-2,2-dimethylcyclopropane carboxylate, (S)-α-carboxamido-3-(2,2-dichlorovinyloxy)benzyl (1R,3R)-3-(2,2-dichlorovinyl)-2,2-dimethylcyclopropane carboxylate, (±)-α-carboxamido-3-phenoxybenzyl (±)-(4-chlorophenyl)isovalerate, (S)-α-carboxamido-3-phenoxybenzyl (±)-(4-chlorophenyl)isovalerate, (S)-α-carboxamido-3-phenoxybenzyl (1R,3R)-3-(2,2-dibromovinyl)-2,2-dimethylcyclopropane carboxylate.

The compounds of the invention may be prepared by reacting a compound of formula:

where Q is halogen, preferably chlorine, with an alcohol of formula:

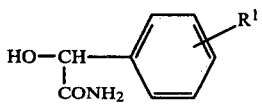 (IV)

optionally in the presence of a base.

Conveniently the above process may be performed by dissolving the alcohol of Formula IV in a suitable solvent in the presence of a base, or the solvent itself may be the base (e.g. pyridine) and adding to the solution a solution of the acid halide of Formula III in a suitable solvent, for example a hydrocarbon solvent, such as benzene or toluene, at a temperature within the range −5° to +30° C., preferably the ambient temperature. Although the reaction may be accelerated or completed by the application of heat, it is often sufficient merely to allow the reaction to proceed at the ambient temperature. The product may be isolated and purified by conventional techniques.

Alternative processes for the preparation of the esters of the invention include for example reaction of the acid of formula:

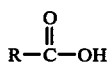 (V)

(optionally in the form of its salt) with a halide of formula

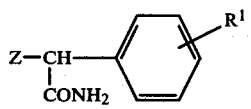 (VI)

or reaction of the acid of Formula V with the alcohol of Formula IV in the presence of a suitable acid catalyst.

Optically active compounds of Formula I may be prepared by reacting together optically active compounds of Formulae III or V with optically active compounds of Formulae IV or VI as appropriate, or by reaction of one optically active compound with a racemate of the other reactant followed by separation of the diastereoisomeric isomers by differential solubility e.g. by fractional crystallisation.

Thus, reaction of the (S)-isomer of an alcohol of Formula IV with the racemic form of a compound of Formula III (e.g. the (±)-cis-form of a compound of Formula III where R is a group of Formula A) to give a pair of diastereoisomers, which for convenience could be termed (+)(S) and (−)(S), and these could be separated by the use of fractional crystallisation techniques.

The alcohols of Formula IV are themselves novel compounds. Compounds of formula:

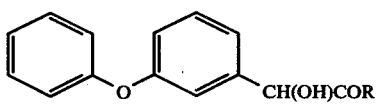 (VII)

wherein R is hydroxy, amino or alkoxy containing from 1 to 4 carbon atoms, and ammonium salts of such compounds wherein R is hydroxy, are particularly useful as intermediates in the preparation of the caboxamidoesters of the invention.

Examples of specific compounds useful as intermediates include:
racemic 3-phenoxymandelic acid,
(S)-3-phenoxymandelic acid,
(R)-3-phenoxymandelic acid,
racemic 3-phenoxymandelamide,
(S)-3-phenoxymandelamide,
(R)-3-phenoxymandelamide,
racemic methyl 3-phenoxymandelate,
methyl (S)-3-phenoxymandelate,
methyl (R)-3-phenoxymandelate, and examples of ammonium salts include the 1-(−)-α-methylbenzylammonium and the d-(+)-α-methylbenzylammonium salts of racemic, (R)- and (S)-3-phenoxymandelic acids.

The compound of formula VII wherein R is OH may be obtained by the hydrolysis of 3-phenoxybenzaldehyde cyanhydrin, and it may be resolved into its constituent (R) and (S)-isomers by conversion to the salt of an optically active amine, for example α-methylbenzylamine. The salts may then be separated by their differential solubility characteristic e.g. by fractional crystallisation.

The hydrolysis of the cyanhydrin is preferably carried out using acid conditions, for example by heating the cyanhydrin with a dilute mineral acid in aqueous alcoholic solution for a period of from about 30 minutes to several hours. The process may be carried out using for example aqueous ethanolic hydrochloric acid at a temperature within the range 65° to 90° C., and may be supplemented by a period of treating the reactants with aqueous caustic alkali solution at a similar temperature. When the hydrolysis is complete the acid obtained may be purified by making a suitable water soluble salt, for example the sodium salt, to separate the acid from water insoluble material, and reprecipitating at pH less than 7 by using a mineral acid.

The compounds of formula VII wherein R is alkoxy as defined may be obtained for example by treating the 3-phenoxymandelic acid with an appropriate alcohol in the presence of an acid catalyst. This process may be conducted at the ambient temperature using for example an excess of the alcohol containing dissolved hydrogen chloride. Alternatively other methods of esterification may be used such as treating the alcohol with 3-phenoxymandelic acid halide in the presence of a base.

The compounds of formula VII wherein R is amino may conveniently be prepared by treating the alkyl esters of 3-phenoxymandelic acid with ammonia under pressure, for example by adding the ester to liquid ammonia at low temperature, and allowing the mixture to warm up to the ambient temperature in a sealed vessel.

The above processes may be used in sequence to convert 3-phenoxybenzaldehyde cyanhydrin to 3-phenoxymandelamide, and this latter compound either as the racemate or as the (R)- or (S)-isomer can be used for example in the preparation of α-carboxamido-3-phenoxybenzyl 3-(2,2-dihalovinyl)-3,3-dimethylcyclopropane carboxylates, which are themselves precursors for the insecticidally active α-cyano-3-phenoxybenzyl 3-(2,2-dihalovinyl)-3,3-dimethylcyclopropane carboxylates.

As stated above the carboxamido esters of this invention are useful as intermediates in the preparation of insecticides, and they are particularly useful in preparing and isolating partially or totally optically resolved isomeric forms of these insecticides. The insecticidal products have the formula:

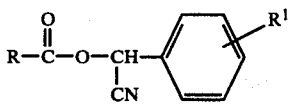

(VIII)

(where R and R[1] are defined as hereinabove) and they may be prepared by dehydration of the novel esters of this invention.

A useful dehydrating agent is a phosphorus oxyhalide, for example, phosphorus oxychloride, and the process is conveniently carried out by bringing a solution of the oxyhalide in a suitable solvent, for example a chlorinated hydrocarbon solvent such as methylene dichloride, into contact for a period of from about 30 minutes to about 30 hours with a solution of the compound of Formula I in a suitable solvent such as for example pyridine, at a temperature within the range −20° to +50° C., preferably within the range −10° to about +20° C.

The dehydration process may be used to convert racemates of Formula I to the racemate of Formula VIII, or it may equally well be used to convert compounds of Formula I in the (R)- or (S)-configuration to the corresponding isomers of the compounds of Formula VIII whilst retaining the stereochemical configuration around the optically active centre. That is the conversion from carboxamido to cyano occurs without racemisation or inversion or loss of optical purity. Thus the process is extremely useful in preparing individual stereochemical isomers of the compounds of Formula VIII.

Thus for example (S)-α-cyano-3-phenoxybenzyl (1R,3R)-3-(2,2-dichlorovinyl)-2,2-dimethylcyclopropane carboxylate may be prepared from (S)-α-carboxamido-3-phenoxybenzyl (1R,3R)-3-(2,2-dichlorovinyl)-2,2-dimethyl-cyclopropane carboxylate.

Other compounds which may be prepared by the dehydration process from the appropriate carboxamidoester of the invention include the following:

(S)-α-cyano-3-phenoxybenzyl (1R,3R)-3-(2,2-dibromovinyl)-2,2-dimethylcyclopropane carboxylate, (S)-α-cyano-3-(2,2-dichlorovinyloxy)benzyl (1R,3R)-3-(3,3-dichlorovinyl)-2,2-dimethylcyclopropane carboxylate, (S)-α-cyano-3-phenoxybenzyl (1R,3R)-chrysanthemate, (S)-α-cyano-3-phenoxybenzyl (±)-2-(4-chlorophenyl)isovalerate, and (S)-α-cyano-3-(2,2-dichlorovinyloxy)benzyl (±)-2-(4-chloro-phenyl)isovalerate, together with the corresponding (R)-α-cyano compounds.

The invention is illustrated by the following Examples, in which Examples 1 to 5 illustrate the preparation of intermediates, and Examples 6 to 8 illustrate the preparation of the carboxamidoesters thermselves. Example 9 illustrates the dehydration of the carboxamidoester to the corresponding nitrile.

EXAMPLE 1

This Example illustrates the preparation of racemic 3-phenoxymandelic acid.

A mixture of 3-phenoxybenzaldehyde cyanhydrin (208 g), ethanol (600 ml) and concentrated hydrochloric acid (400 ml) was kept at the ambient temperature for 24 hours, after which it was concentrated by evaporation under reduced pressure. 2 N Sodium hydroxide solution (500 ml) was added to the residue and the mixture heated at 80° C. for one hour, cooled, concentrated hydrochloric acid (250 ml) added to it, and the resultant mixture heated at 80° C. for a further hour. The volatile portion was removed by evaporation under reduced pressure and the residue stirred with a solution of sodium bicarbonate (60 g) in water (60 g). The aqueous solution was decanted from the undissolved oil, stirred with activated charcoal, filtered, and the filtrate acidified with hydrochloric acid. The precipitated solid was collected by filtration and dried to yield racemic 3-phenoxymandelic acid, m.p. 131° C.

EXAMPLE 2

This Example illustrates the resolution of racemic 3-phenoxymandelic acid.

l-(−)-α-Methylbenzylamine (21.0 g) was added to a solution of racemic 3-phenoxymandelic acid (67.0 g) in isopropyl alcohol (700 ml) and the mixture kept for 24 hours at the ambient temperature. The solid precipitate was collected by filtration, (the filtrate kept—see below) and recrystallised twice from isopropyl alcohol (200 ml) to yield the l-(−)-α-methylbenzylammonium salt of (S)-3-phenoxymandelic acid, m.p. 153° C. This was then shaken with a mixture of diethyl ether (150 ml) and 5 N hydrochloric acid (25 ml), the ether layer separated, washed with water, dried over anhydrous magnesium sulphate and concentrated by evaporation and the ether under reduced pressure to yield a residue of solid (S)-3-phenoxymandelic acid, m.p. 110°-112° C. $[\alpha]_D^{25}+85°$ (C, 1,5, methanol).

The isopropyl alcohol solution obtained as a filtrate in the above process was concentrated by evaporation under reduced pressure until reduced to a volume of 50 ml. This was then shaken with 2 N hydrochloric acid (150 ml) and the resultant solid precipitate collected by filtration. This solid (impure (R)-3-phenoxymandelic acid) was dissolved in isopropyl alcohol (400 ml) and d-(+)-α-methylbenzylamine (17.0 g) added to the solution. After keeping the mixture at the ambient temperature for a period of 24 hours the solid precipitate was collected by filtration, and recrystallised twice from isopropyl alcohol (200 ml) to yield the d-(+)-α-methylbenzyl-ammonium salt of (R)-3-phenoxymandelic acid, m.p. 154° C. Free (R)-3-phenoxymandelic acid was otained from this salt by treatment in the manner described above for the isolation of the (S)-isomer. The (R)-isomer had m.p. 112° C., $[\alpha]_D^{25}-84°$ (C, 1.0, methanol).

EXAMPLE 3

This Example illustrates the preparation of (S)-3-phenoxymandelamide.

(S)-3-Phenoxymandelic acid (13.0 g) was added to a solution of dry hydrogen chloride (15.0 g) in methanol (100 ml) and the solution thus obtained kept at the ambient temperature for 24 hours after which period the volatile portion was evaporated yielding methyl (S)-3-phenoxymandelate as a residual oil. This was then added to liquid ammonia (20 ml) in a pressure vessel which was then sealed and temperature of the mixture allowed to rise to the ambient temperature over a period of 24 hours. The vessel was then opened and the excess of ammonia allowed to evaporate. The residual material was stirred with water and the solid collected by filtration, and recrystallised from benzene (70 ml) to yield impure (S)-3-phenoxymandelamide, m.p. 93° C. $[\alpha]_D^{25}+25.4°$ (C, 2.0, methanol), (approximately 80% optically pure).

Optically pure material was obtained using the following procedure:

A suspension of impure (S)-3-phenoxymandelamide (7.5 g) in a mixture of benzene (150 ml) and n-butanol (6 ml) was stirred at 25° C. for 30 minutes. The undissolved solid was separated by filtration and the filtrate was evaporated. The residue was recrystallised from benzene to give optically pure (S)-3-phenoxymandelamide, m.p. 94° C., $[\alpha]_D^{25}+30°$ (c. 2.0, methanol).

Further optically pure (S)-3-phenoxymandelate was obtained by repeating the above purification procedure using the undissolved solid separated from the benzene/n-butanol mixture.

EXAMPLE 4

By using a procedure similar to that illustrated in the previous Example, (R)-3-phenoxymandelamide, m.p. 94° C., $[\alpha]_D^{25}-30°$ (C. 2, methanol) was obtained starting from (R)-3-phenoxymandelic acid, via the methyl ester and after final purification of the initially isolated 80% optically pure (R)-3-phenoxymandelamide, m.p. 93° C., $[\alpha]_D^{25}-25.3°$ (c. 2.0, methanol).

EXAMPLE 5

By using a procedure similar to that illustrated in the two previous Examples, racemic 3-phenoxymandelamide, m.p. 109° C., was obtained via racemic methyl 3-phenoxymandelate (m.p. 71° C.).

EXAMPLE 6

This Example illustrates the preparation of (S)-α-carboxamido-3-phenoxybenzyl (1R,3R)-3-(2,2-dichlorovinyl)-2,2-dimethylcyclopropane carboxylate.

A solution of (1R,3R)-3-(2,2-dichlorovinyl)-2,2-dimethylcyclopropane carboxylic acid chloride (0.45 g) in benzene (2.0 ml) is added at 5° C. to a solution of (S)-3-phenoxymandelamide (0.5 g) in pyridine (1.0 ml), and the mixture is kept at the ambient temperature for 24 hours. After this period the mixture is acidified with dilute hydrochloric acid, the benzene layer separated, washed with water and with aqueous sodium bicarbonate solution, dried and concentrated by evaporation of the benzene under reduced pressure. The residual oil is treated with cyclohexane (10 ml), and the precipitated solid collected by filtration and dried to yield (S)-α-carboxamido-3-phenoxybenzyl (1R,3R)-3-(2,2-dichlorovinyl)-2,2-dimethylcyclopropane carboxylate, m.p. 131° C.

EXAMPLE 7

This Example also illustrates the preparation of (S)-α-carboxamido-3-phenoxybenzyl (1R,3R)-3-(2,2-dichloro-vinyl)-2,2-dimethylcyclopropane carboxylate.

A solution of (1R,3R)-3-(2,2-dichlorovinyl)-2,2-dimethylcyclopropane carboxylic acid chloride (0.44 g) in benzene (2.0 ml) was added to a solution of racemic 3-phenoxymandelamide (0.5 g) in pyridine (1.0 ml) at 5° C. The mixture was kept for 24 hours at the ambient temperature and then acidified with dilute hydrochloric acid. The benzene layer was separated and washed with aqueous sodium bicarbonate solution. After concentration of the benzene solution by evaporation under reduced pressure to a volume of 1.0 ml, cyclohexane (3.0 ml) was added and the mixture kept at the ambient temperature. A solid (m.p. 124°) was precipitated on keeping, and this was collected by filtration and recrystallised from a mixture of benzene and cyclohexane to yield (S)-α-carboxamido-3-phenoxybenzyl (1R,3R)-3-(2,2-dichlorovinyl)-2,2-dimethylcyclopropane carboxylate, m.p. 131° C., identical with the product obtained in the previous Example.

The benzene/cyclohexane mother liquors contained impure (R)-α-carboxamido-3-phenoxybenzyl (1R,3R)-3-(2,2-dichlorovinyl)-2,2-dimethylcyclopropane carboxylate.

EXAMPLE 8

The procedure of the previous Example was used to prepare (S)-α-carboxamido-3-phenoxybenzyl (1R,3R)-3-(2,2-dichlorovinyl)-2,2-dimethylcyclopropane carboxylate, m.p. 131° C., identical with the product obtained in the previous Example, from racemic cis-3-(2,2-dichlorovinyl)-2,2-dimethylcyclopropane carboxylic acid chloride (0.65 g) and (S)-3-phenoxymandelamide (0.5 g). The benzene/cyclohexane mother liquors contained impure (S)-α-carboxamido (1R,3R)-3-(2,2-dichlorovinyl)-2,2-dimethylcyclopropane carboxylate.

EXAMPLE 9

This Example illustrates the preparation of (S)-α-cyano-3-phenoxybenzyl (1R,3R)-3-(2,2-dichlorovinyl)-2,2-dimethylcyclopropane carboxylate.

A solution of phosphorus oxychloride (0.33 g) in methylene dichloride (1.0 ml) was added dropwise over a period of 5 minutes to a solution of (S)-α-carboxamido-3-phenoxybenzyl (1R,3R)-3-(2,2-dichlorovinyl)-2,2-dimethylcyclopropane carboxylate (0.5 g) in pyridine (1.5 ml) whilst the temperature was maintained at −5° C. The mixture was then stirred at 0° C. for one hour, after which it was diluted with benzene and poured into dilute hydrochloric acid. The benzene layer was separated, washed with water and with aqueous sodium bicarbonate solution, dried and concentrated by evaporation of the benzene to yield a residue of (S)-α-cyano-3-phenoxybenzyl (1R,3R)-3-(2,2-dichlorovinyl)-2,2-dimethylcyclopropane carboxylate, m.p. 54° C., which on recrystallisation from petroleum ether gave the pure material m.p. 57° C.

I claim:

1. (S)-α-carboxamido-3-(2,2-dichlorovinyloxy)benzyl (1R,3R)-3-(2,2-dichlorovinyl)-2,2-dimethylcyclopropane carboxylate.

* * * * *